(12) United States Patent
Goetz et al.

(10) Patent No.: US 11,150,492 B2
(45) Date of Patent: Oct. 19, 2021

(54) OPHTHALMIC DEVICE WITH AUTO-ACCOMMODATION

(71) Applicant: Verily Life Sciences LLC, South San Francisco, CA (US)

(72) Inventors: Georges Goetz, Mountain View, CA (US); Eliezer Glik, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 147 days.

(21) Appl. No.: 16/379,214

(22) Filed: Apr. 9, 2019

(65) Prior Publication Data

US 2019/0353934 A1 Nov. 21, 2019

Related U.S. Application Data

(60) Provisional application No. 62/672,798, filed on May 17, 2018.

(51) Int. Cl.
| | |
|---|---|
| *G02C 7/04* | (2006.01) |
| *G02C 11/00* | (2006.01) |
| *A61F 2/16* | (2006.01) |
| *A61F 2/48* | (2006.01) |

(52) U.S. Cl.
CPC .............. *G02C 7/04* (2013.01); *A61F 2/1624* (2013.01); *G02C 7/041* (2013.01); *G02C 11/10* (2013.01); *A61F 2002/482* (2013.01)

(58) Field of Classification Search
CPC ............ G02C 7/02; G02C 7/04; A61F 2/1624
USPC .............. 351/159.02, 159.03, 159.39, 159.4; 623/6.22
See application file for complete search history.

(56) References Cited

U.S. PATENT DOCUMENTS

| | | |
|---|---|---|
| 7,041,133 B1 | 5/2006 | Azar |
| 8,545,555 B2 | 10/2013 | Berge |
| 2003/0018383 A1 | 1/2003 | Azar |

(Continued)

FOREIGN PATENT DOCUMENTS

| | | |
|---|---|---|
| DE | 102007948859 A1 | 4/2009 |
| WO | 2007131014 A2 | 11/2007 |

OTHER PUBLICATIONS

International Search Report & Written Opinion for corresponding International Application No. PCT/US2019/032529, dated Aug. 1, 2019, 13 pages.

*Primary Examiner* — Darryl J Collins
(74) *Attorney, Agent, or Firm* — Christensen O'Connor Johnson Kindness PLLC (57) ABSTRACT

An ophthalmic device includes an accommodating optic having adjustable optical power, an optical tap positioned within a vision of an eye when the ophthalmic device is mounted in or on the eye, an image sensor positioned outside of a foveal vision of the eye when the ophthalmic device is mounted in or on the eye, and a controller coupled to the accommodating optic and the image sensor. The optical tap redirects a portion of the vision light that passes through the accommodating optic as tapped light. The image sensor is aligned to receive the tapped light from the optical tap and adapted to generate image data indicative of a focus of the vision light in response to the tapped light. The controller is adapted to generate an accommodation control signal that manipulates the adjustable optical power of the accommodating optic based upon the image data.

25 Claims, 7 Drawing Sheets

(56) References Cited

U.S. PATENT DOCUMENTS

| | | |
|---|---|---|
| 2007/0260307 A1 | 11/2007 | Azar |
| 2012/0092613 A1* | 4/2012 | Azar .................. A61F 2/16 |
| | | 351/159.03 |
| 2012/0127422 A1* | 5/2012 | Tian .................. G02B 7/365 |
| | | 351/158 |
| 2016/0324628 A1 | 11/2016 | Gupta et al. |
| 2017/0020661 A1 | 1/2017 | Cheatham, III et al. |

* cited by examiner

OPHTHALMIC DEVICE WITH AUTO-ACCOMMODATION

CROSS-REFERENCE TO RELATED APPLICATIONS

This application claims the benefit of U.S. Provisional Application No. 62/672,798, filed May 17, 2018, which is hereby incorporated by reference in its entirety.

TECHNICAL FIELD

This disclosure relates generally to ophthalmic devices, and in particular, relates to accommodating ophthalmic devices.

BACKGROUND INFORMATION

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, the effectiveness of the ciliary muscle degrades due to hardening of the lens. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages. Techniques and devices that can help individuals offset the effects of Presbyopia are increasingly in demand.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method for auto-accommodation control of an ophthalmic device via optically tapping vision light, such as foveal vision light, are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Variable power ophthalmic devices that offset the effects of Presbyopia or other ocular diseases are being developed. Such ophthalmic devices include variable power intraocular lenses (IOLs), variable power contact lenses, variable power glasses/visor/head wearable display, etc. The variable optical power provided by the active optic of these ophthalmic devices help a user with diminished capacity to adjust their focus (i.e., accommodate) and bring objects of variable focal depth into focus. Determining how much accommodation a user needs for a given activity and therefore how much to adjust the variable power of the active optic is a challenge.

Candidates for solving this accommodation control problem include (1) directly sensing the electrical signals of the ciliary muscle using electromyography techniques, (2) gaze direction or convergence sensing, (3) indirect sensing from pupillary contraction, and (4) sensing the mechanical reflexes/deformation of the ciliary muscle or capsular sack. These approaches focus on extracting a signal from the patient that indicates the intent to accommodate. However, the human visual system is dominated by a very small region of the visual field, which is the portion of the image projected on the fovea of the retina, and people subconsciously bring in sharp focus the object located in their foveal direction of gaze. Therefore, sensing the distance to an object in the foveal direction of gaze is an alternative to sensing approaches which rely on physiological changes in the eye.

The techniques disclosed herein use an optical measure of the distance to an object located in a user's vision, such as the foveal direction of gaze (foveal vision), by performing a sampling of the light field emitted by the object. Phase-detect autofocus (PDAF) techniques, or otherwise, are then applied to this sampled vision light to obtain a measure of the level of defocus of the vision light and thereby generate an accommodation control signal to provide feedback control over an accommodating optic to bring the object into focus.

Figure 1:
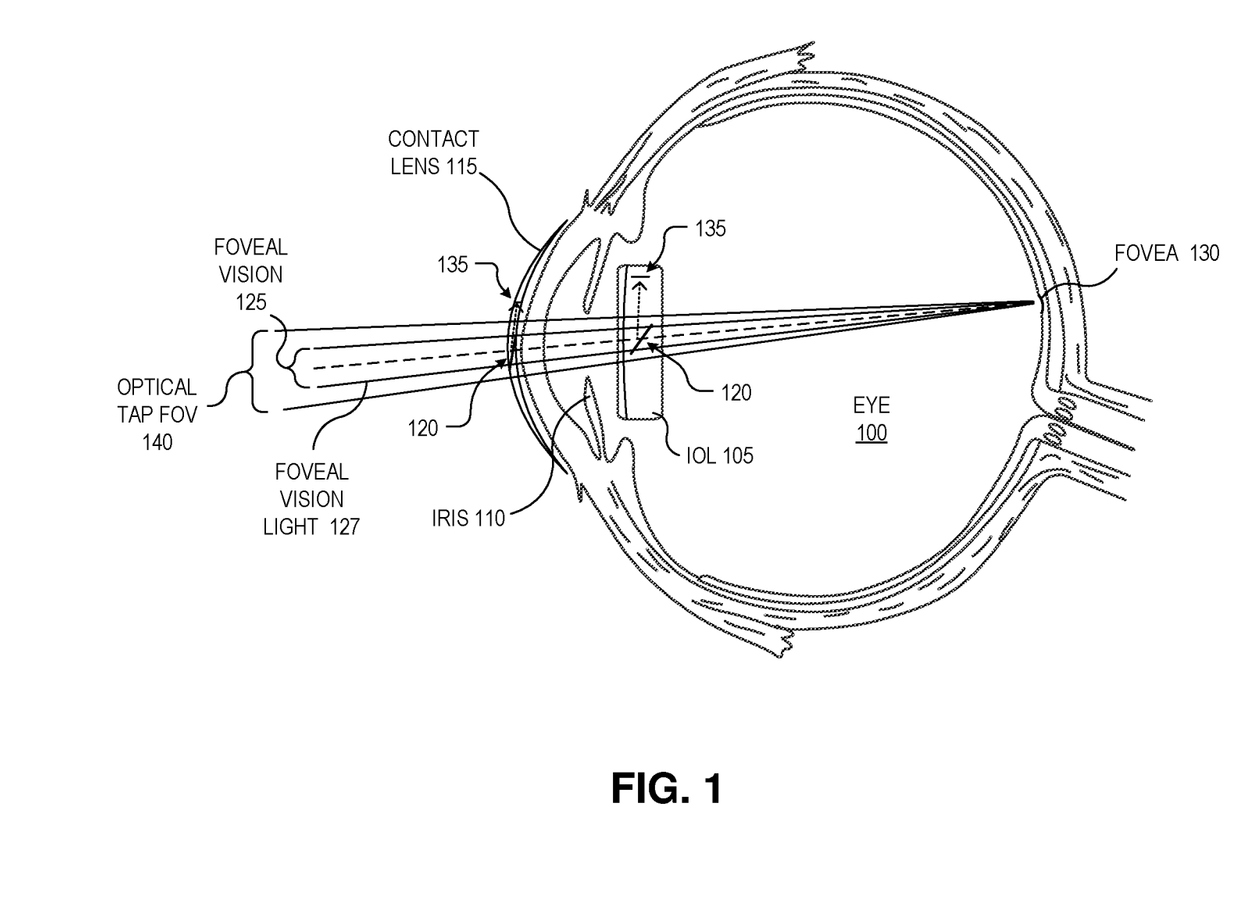
FIG. 1 is an illustration of various ophthalmic devices mounted in or on an eye, in accordance with an embodiment of the disclosure.

FIG. 1 is an illustration of various ophthalmic devices mounted in or on an eye 100, which may leverage the auto-accommodation techniques described herein. For example, the ophthalmic device may be implemented as an accommodating intraocular lens (IOL) 105 mounted into eye 100. In the illustrated embodiment, IOL 105 is implanted into the posterior chamber of eye 100 behind iris 110. However, in other embodiments, IOL 105 may be implanted into other positions (e.g., anterior chamber) of eye 100, or even have subcomponents distributed over multiple locations in, on, or surrounding (e.g., under the sclera) eye 100. In some embodiment, ancillary/subcomponents may be tethered to the main accommodating lens component. Alternatively, the ophthalmic device may be implemented as an accommodating contact lens 115 that is mounted over the cornea of eye 100. In yet other embodiments (not illustrated), the ophthalmic device may include glasses, goggles, a visor, or other eyewear. Although FIG. 1 illustrates both IOL 105 and contact lens 115, it should be appreciated that in practice a user may only use a single ophthalmic device at a time.

Each of the ophthalmic devices includes an optical tap 120 positioned within the user's vision (illustrated as foveal vision 125) to tap a small portion of the foveal vision light 127 projected onto fovea 130 and redirect this "tapped light" to an image sensor 135 peripherally positioned outside the user's foveal vision 125. Image sensor 135 generates image data in response to the tapped light that is indicative of a focus of the foveal vision. A controller (e.g., see FIGS. 2A or 2B) is coupled to image sensor 135 to receive the image data and uses PDAF principles to generate the accommodation control signal.

The auto-accommodation techniques described herein directly analyze the user's foveal vision light as compared to inferences from physiological changes in the eye. Fovea 130, which is responsible for foveal vision 125, has a field of view (FOV) of approximately two and a half degrees in the typical human eye 100. In one embodiment, optical tap 120 is designed to have a FOV 140 that is approximately two times (e.g., five degrees) or less of foveal vision 125. For example, in various embodiments, FOV 140 of optical tap 120 may be slightly larger or slightly smaller than the foveal FOV (foveal vision 125). Optical tap 120 within IOL 105 or contact lens 115 may have a cross-sectional dimension that is less than 5 mm and may even have a cross-sectional dimension of approximately 2 mm in the example of IOL 105. Of course, other dimensions and FOVs may be implemented. In some embodiments, optical tap 120 may be positioned just outside the user's foveal vision or straddle the boundary of the user's foveal vision.

Figure 2A:
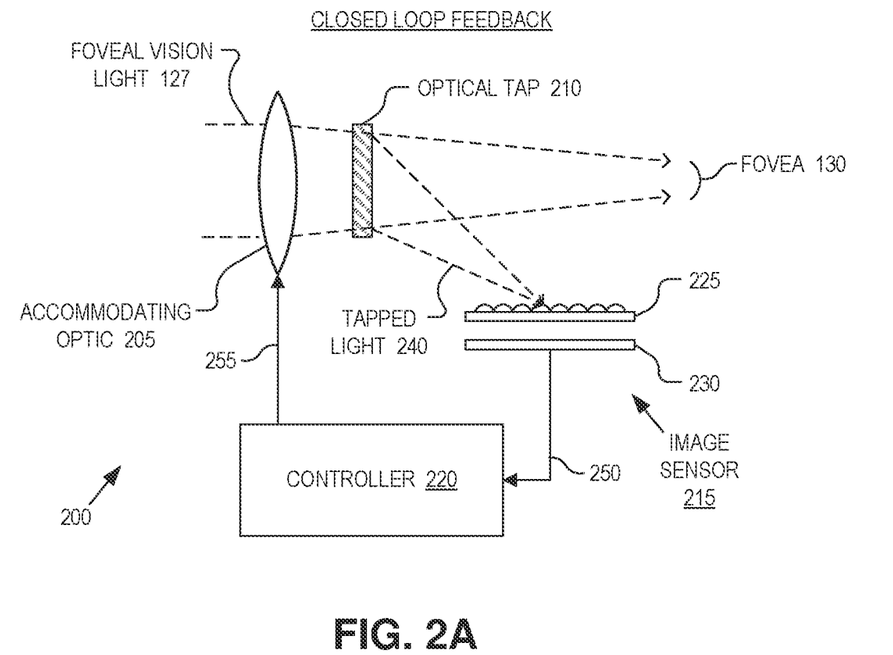
FIG. 2A is a functional block diagram of components of an ophthalmic device arranged to provide closed loop feedback control over an accommodating optic using an optical tap, in accordance with an embodiment of the disclosure.
Figure 2B:
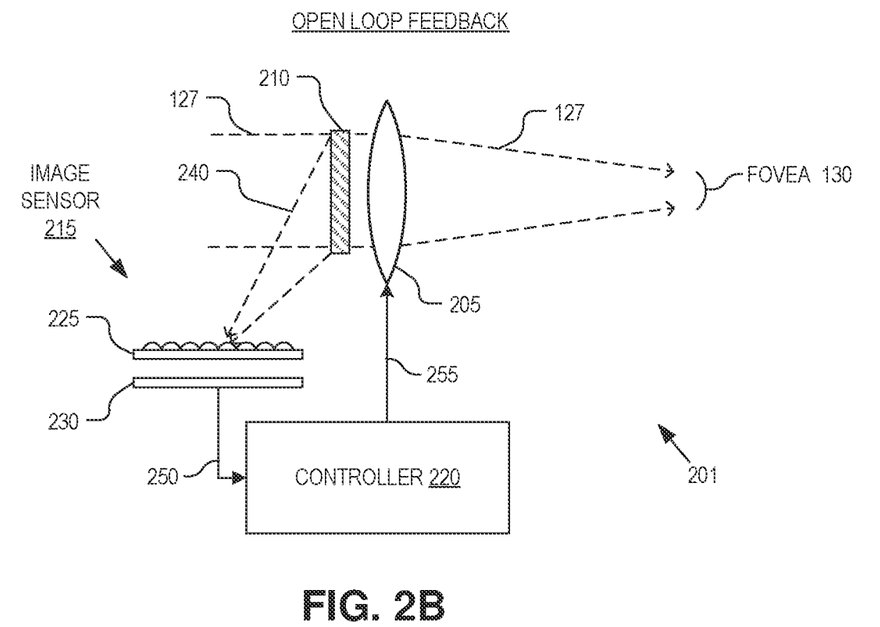
FIG. 2B is a functional block diagram of components of an ophthalmic device arranged to provide open loop feedback control over an accommodating optic using an optical tap, in accordance with an embodiment of the disclosure.

FIGS. 2A and 2B are functional block diagrams illustrating relevant components of ophthalmic devices arranged to provide feedback control over an accommodating optic using an optical tap positioned in a user's foveal vision 125, in accordance with embodiments of the disclosure. FIG. 2A illustrates an ophthalmic device 200 that includes an accommodating optic 205, an optical tap 210, an image sensor 215, and a controller 220. The illustrated embodiment of image sensor 215 includes a microlens array 225 and a photosensor array 230.

FIG. 2A illustrates a closed loop arrangement of the components where optical tap 210 is positioned along the optical path of foveal vision light 127 relative to accommodating optic 205 such that foveal vision light 127 passes through accommodating optic 205 prior to passing though optical tap 210. In other words, tapped light 240 is redirected after passing through accommodating optic 205. In contrast, FIG. 2B illustrates similar components of an ophthalmic device 201 arranged into an open loop feedback arrangement wherein foveal vision light 127 passes through optical tap 210 prior to reaching accommodating optic 205. In this arrangement, tapped light 240 is redirected prior to passing through accommodating optic 205.

During operation, foveal vision light 127 passes through accommodating optic 205 prior to its incidence upon fovea 130. Accommodating optic 205 has adjustable optical power, which is manipulated by controller 220 to aid with accommodation of the user's vision to bring objects of variable focal distance into focus. Accommodating optic 205 may be implemented using a variety technologies including a liquid crystal lens, an electrowetting lens, a mechanically adjustable lens structure (e.g., microelectromechanical system, etc.), electrochromic devices, other electro-optic devices, or otherwise.

Controller 220 includes logic for orchestrating the operation of the other electrical components. For example, in the illustrated embodiment, controller 220 is coupled to photosensor array 230 of image sensor 215 to receive image data 250 therefrom and further coupled to accommodating optic 205 to manipulate its adjustable optical power with accommodation control signal 255. The logic of controller 220 may be implemented entirely in hardware (e.g., application specific integrated circuit, field programmable gate array, etc.), entirely in software/firmware instructions stored in a memory unit that is executed by a microcontroller, or by a combination of both hardware and software. In one embodiment, controller 220 may implement a phase-detect autofocus (PDAF) scheme. In one embodiment, controller 220 may implement a contrast-detect autofocus (CDAF) scheme. In general, a CDAF scheme seeks to increase image contrast, which is correlated with correct image focus. The CDAF scheme may be more suitable for the closed loop feedback arrangement illustrated in FIG. 2A.

Figure 3A:
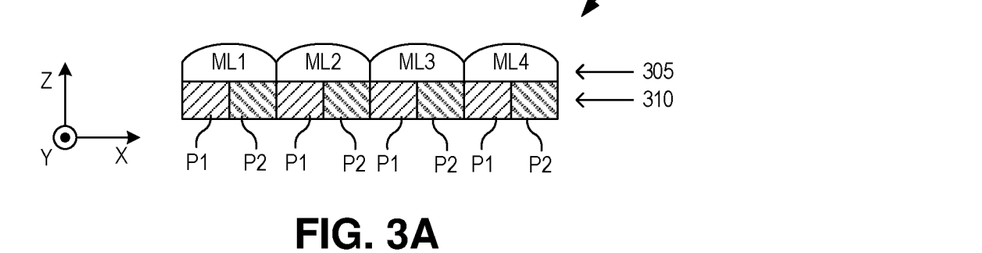
FIG. 3A is a cross-sectional illustration of an image sensor including linear arrays of microlenses and photosensors that generate image data indicative of a focus of foveal vision light, in accordance with an embodiment of the disclosure.
Figure 3B:
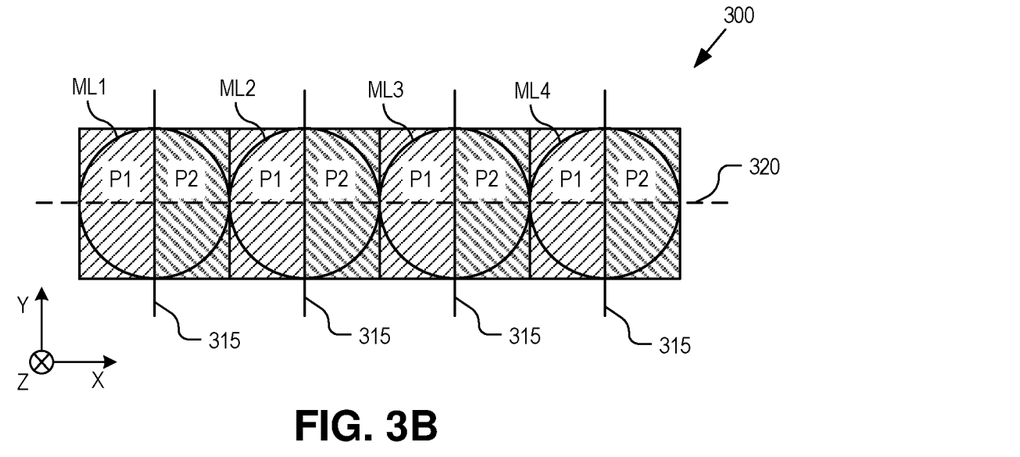
FIG. 3B is a plan view illustration of the image sensor including linear arrays of microlenses and photosensors, in accordance with an embodiment of the disclosure.

FIGS. 3A & 3B illustrate different views of an image sensor 300 that generates image data 250 indicative of a focus of foveal vision light 127, in accordance with an embodiment of the disclosure. Image sensor 300 is one possible implementation of image sensor 215 in FIGS. 2A and 2B. The illustrated embodiment of image sensor 300 includes a linear array 305 of microlenses ML1-ML4 and a linear array 310 of photosensors P1 and P2.

In the illustrated embodiment, a pair of photosensors P1 and P2 is placed behind each microlens ML1-ML4, so that the axis 315 along which they split the given microlens ML1-ML4 is orthogonal to the axis 320 along which the linear array 310 of microlens ML1-ML4 is laid out. As a result, there are two photodiodes P1 and P2 per microlens ML1-ML4 and arrays 305 and 310 are aligned parallel to each other along axis 320. In one embodiment, the image data obtained from the even photosensors P2 is cross-correlated with the image data obtained from the odd photosensors P1 in the array 310. The distance from zero at which the peak in the cross-correlogram occurs is a direct, linear measure of the optical defocus present in foveal vision light 127. In other words, the relative intensities of the light incident upon the photosensors in array 310 correlates to focus/defocus of foveal vision light 127, which can then be used to generate accommodation control signal 255 for manipulating the optical power of accommodating optic 205. As mentioned above, this feedback control may be arranged into a closed loop (FIG. 2A) or open loop (FIG. 2B) feedback control circuit.

The photosensors may be implemented using a variety of technologies. For example, photosensors may be photodiodes, charged coupled devices, photo-resistors, or other photoactive devices. Although FIGS. 3A and 3B illustrates four microlenses ML1-ML4 within array 305 and two photosensors P1 and P2 aligned behind each microlens, it should be appreciated that image sensor 300 may be implemented with as few as two microlenses to many more microlenses. Similarly, the number of photosensors per microlens may be two or more. The specific number, size, pitch, and form factor of microlenses in array 310 may vary according to design needs. However, in practice, it is expected that 8 to 20 microlenses should provide adequate diopter control resolution for a variety of ophthalmic applications though more or less may be implemented.

Figure 3C:
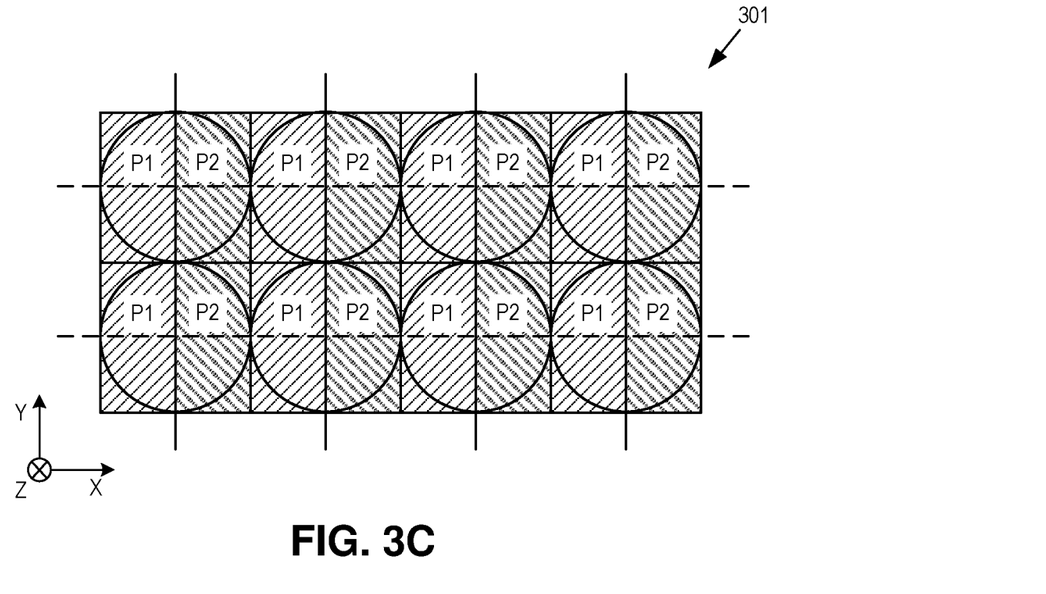
FIG. 3C is a plan view illustration of an image sensor including stacked linear arrays of microlenses and photosensors, in accordance with an embodiment of the disclosure.

FIG. 3C illustrates an image sensor 301 implementation that includes stacked linear arrays of microlenses and photosensors. Stacking multiple linear arrays (e.g., two or more), eases the alignment tolerances between optical tap 210 and the image sensor 215. A switching circuit or integrating/combining circuit (not illustrated) may be coupled to the photosensor outputs of each stacked row to select the row with the best optical alignment or combine the output image data of multiple rows.

Figure 4A:
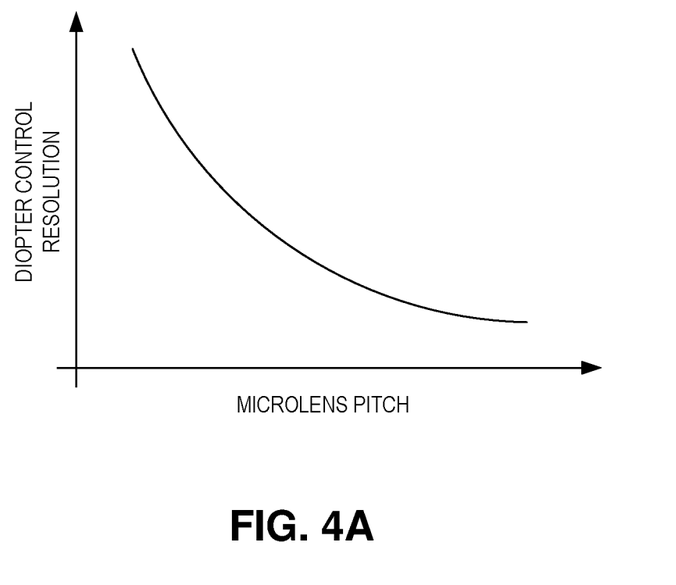
FIGS. 4A and 4B are charts illustrating the influence of microlens pitch on diopter control and illumination sensitivity, respectively, in accordance with embodiments of the disclosure.
Figure 4B:
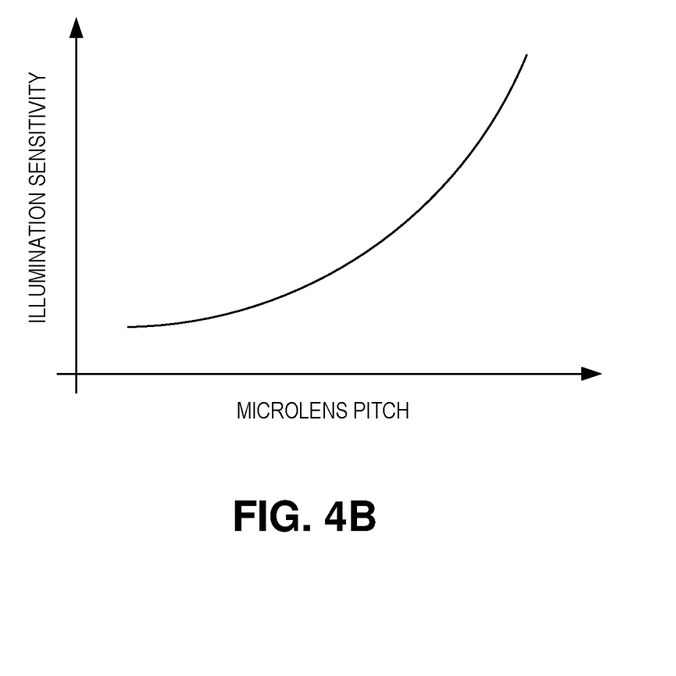

FIGS. 4A and 4B are charts illustrating the tradeoffs of varying the number of microlenses (and by extension photosensors) by increasing the separation pitch between adjacent microlenses. As illustrated in FIG. 4A, with increasing pitch (i.e., larger and fewer microlenses), diopter control resolution decreases. However, as illustrated in FIG. 4B, an increasing pitch of microlenses provides improved low ambient light sensitivity. Appropriate selection of these tradeoffs should be made for the given application (e.g., contact lens, IOL, general purpose usage, specialized usage, mostly day vs mostly night usage, mostly indoor vs mostly outdoor usage, etc.).

As discussed above in connection with FIGS. 2A and 2B, optical tap 210 is positioned within the optical path of foveal vision light 127 to redirect a portion of foveal vision light 127 to image sensor 215 as tapped light 240. Optical tap 210 may be implemented using a diffractive optic (e.g., diffraction grating, hologram, volumetric grating, etc.), a refractive optic, or a specular optic. These optics may operate in either a transmissive mode or a reflection mode, but in either mode, optical tap 210 is partially transmissive or partially reflective so as to pass the majority of foveal vision light 127 to fovea 130. For example, in various embodiments, less than 10% of incident foveal vision light 127 is redirected as tapped light 240 by optical tap 210

In various embodiments, optical tap 210 is focused at infinity to bring collimated foveal vision light 127 received from the ambient environment to a focus on microlens array 225. Accordingly, in various embodiments, optical tap 210 not only redirects or bends foveal vision light 127 but also includes fixed optical power for focusing tapped light 240. In the case of a diffractive optic, redirection may be achieved with a linear phase tilt. The optical power is applied to tapped light 240 whereas the foveal vision light 127 that passes through optical tap 210 to fovea 130 substantially does not experience optical power from optical tap 210. In some embodiments, optical tap 210 imparts optical power to correct for aberrations in the cornea of eye 100 and/or aberrations in a resting or default state of accommodating optic 205. In the case of a diffractive optic, the optical power may be applied to tapped light 240 as a quadratic phase modulation applied on top of the linear phase tilt. Optionally, higher order correction terms may also be written into a diffractive optic implementation for optical tap 210.

In various configurations, microlens array 225 is designed according to the desired sensitivity to defocus, and the parameters of interest include pitch and effective focal length (from which the radius of curvature of the microlenses, specified during microfabrication, derives), as well as the number of microlenses in the array. For example, if six linearly spaced control levels of accommodation are desired for an ophthalmic device over a range of achievable optical powers of 0-5 diopters, the sensitivity to defocus is 1 diopter. The pitch of microlens array 225 derives from this target sensitivity. For a sensitivity to defocus of x diopters, the size of the point spread function (PSF) of the optical system on the plane of microlens array 225 should be calculated. The microlenses are then designed so that their pitch is smaller or equal to the Nyquist sampling frequency limit of the PSF defocused by n diopters (e.g., for a 10 micrometers defocused spot, the microlens pitch may be 5 microns or smaller). A pitch at the Nyquist sampling frequency may be desirable as it should increase photocurrents obtained in each photosensor of photosensor array 230. In one embodiment, the effective focal length of the microlenses is chosen so that the numerical aperture of the microlens matches the numerical aperture of optical tap 210.

FIGS. 5A-D illustrate various configurations and layouts for the optical tap and image sensor, in accordance with embodiments of the disclosure. As illustrated all embodiments may operate in open or closed loop feedback configurations based upon the placement of accommodating optic 205 relative to the optical tap in the optical path of foveal vision light 127.

Figure 5A:
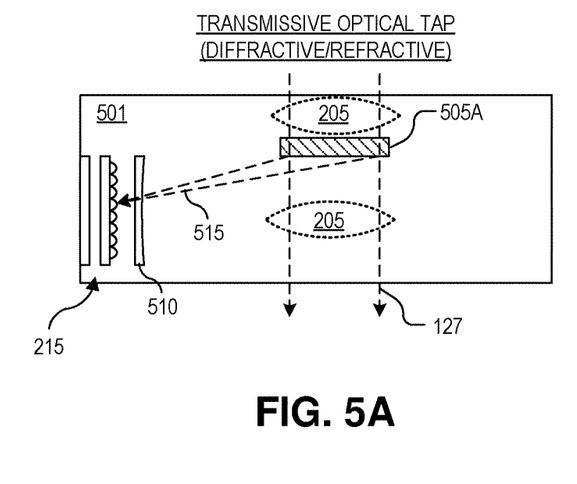
FIG. 5A illustrates a transmissive (diffractive or refractive) configuration of an optical tap, in accordance with an embodiment of the disclosure.

FIG. 5A illustrates a transmissive (diffractive or refractive) configuration 501 for an optical tap 505A, in accordance with an embodiment of the disclosure. In the illustrated embodiment, the plane of the image sensor is peripherally offset from foveal vision light 127 and orthogonally oriented relative to the plane of optical tap 505A. In one embodiment, optical tap 505A is programmed or otherwise includes the optical power for focusing tapped light 515, as described above. In yet another embodiment, a separate lens element 510 is positioned in the optical path of tapped light 515. Although lens element 510 is only illustrated in FIG. 5A so as not to clutter the other figures, it may be optionally included in any of the illustrated configurations in lieu of, or in addition to, incorporating optical power into the optical tap itself.

Figure 5B:
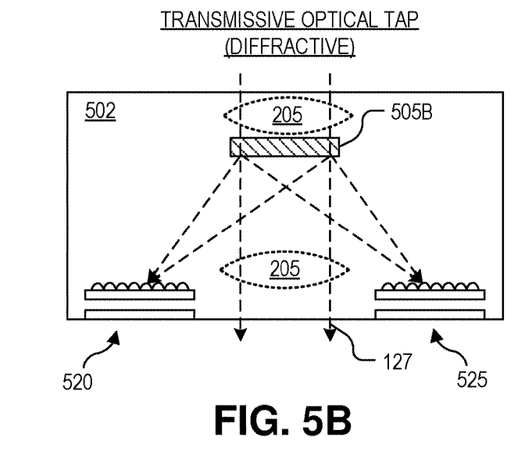
FIG. 5B illustrates a transmissive diffractive configuration of an optical tap that leverages positive and negative diffraction orders, in accordance with an embodiment of the disclosure.

FIG. 5B illustrates a transmissive diffractive configuration 502 for an optical tap 505B that leverages positive and negative diffraction orders, in accordance with an embodiment of the disclosure. Configuration 502 may be selected to ease the constraints on the diffractive element by permitting positive and negative diffraction orders and capturing tapped light from both orders. Accordingly, configuration 502 uses an image sensor that has two sensor submodules 520 and 525 physically offset from each other. In the illustrated embodiment, the plane of optical tap 505B is substantially parallel to the planes of the sensor submodules 520 and 525.

Figure 5C:
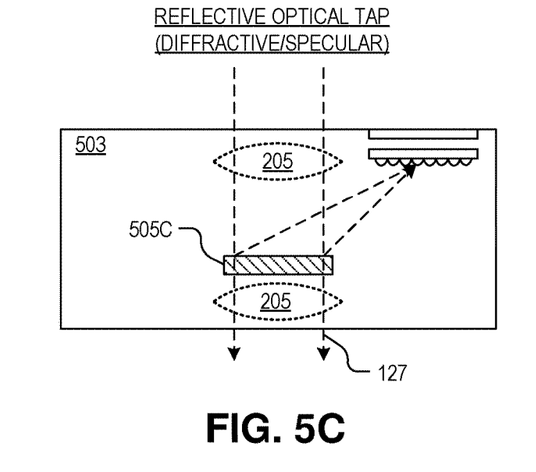
FIG. 5C illustrates a reflective (diffractive or specular) configuration of an optical tap, in accordance with an embodiment of the disclosure.

FIG. 5C illustrates a reflective (diffractive or specular) configuration 503 for an optical tap 503, in accordance with an embodiment of the disclosure. In configuration 505C, optical tap 505C may be implemented with a diffractive optic operating in a reflection mode, or a partially reflective (specular) optic (e.g., beam splitter, dichroic mirror, etc.).

Figure 5D:
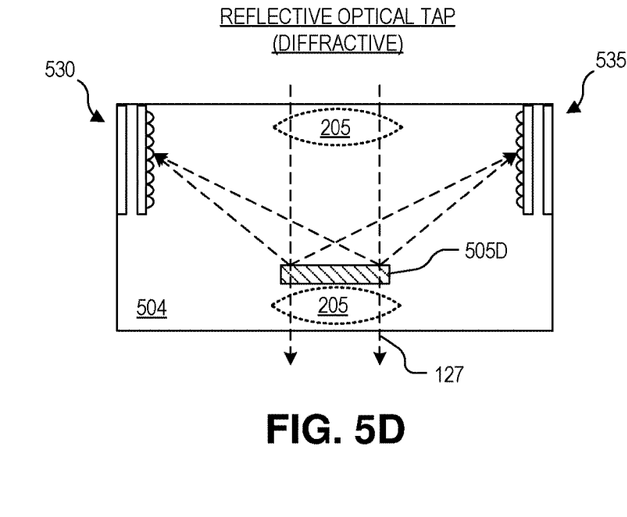
FIG. 5D illustrates a reflective diffractive configuration of an optical tap that leverages positive and negative diffraction orders, in accordance with an embodiment of the disclosure.

FIG. 5D illustrates a reflective diffractive configuration 504 for an optical tap 505D that leverages positive and negative diffraction orders, in accordance with an embodiment of the disclosure. Configuration 504 operates in a similar manner to configuration 502 except that optical tap 505D is a reflective diffractive optic and sensor modules 530 and 535 are orientated orthogonal to optical tap 505D.

The optical taps described herein operate to redirect a portion (e.g., less than 10%) of the foveal vision light 127 towards an image sensor. In some embodiments, the optical taps are designed to redirect a fraction of the incident light over a broad visible spectrum. In yet other embodiments, the optical tap is a notch filter tuned to redirect a fraction of the incident light over a narrow spectrum. For example, in one embodiment, the optical tap is a diffraction grating or dichroic filter tuned to redirect wavelengths coinciding with an absorption band of M-cone photoreceptor cells in fovea 130 while substantially not redirecting other visible spectrum wavelengths. M-cone photoreceptor cells are the medium wavelength photoreceptors in the human eye that are sensitive to green light centered around the 530 nm wavelength. Human eyes tend to be most sensitive to the medium wavelength associated with green. Accordingly, redirecting a fraction of the green wavelength (e.g., 535 nm-545 nm) may have the least detrimental effect on a user's vision.

Figure 6:
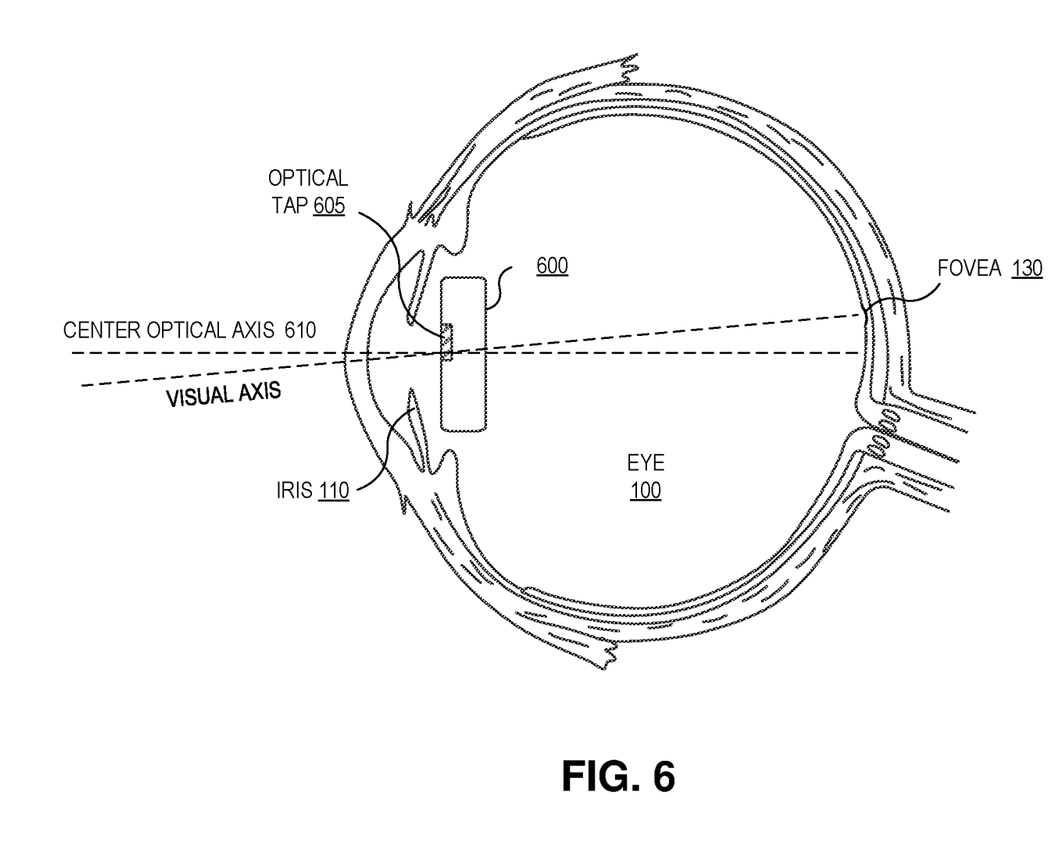
FIG. 6 is a cross-sectional illustration of an ophthalmic device having an optical tap disposed offset from a center optical axis of an eye to leverage a natural reflex of an iris to ambient light to reduce a dynamic range of illumination of the tapped light, in accordance with an embodiment of the disclosure.

FIG. 6 is a cross-sectional illustration of an ophthalmic device 600 having an optical tap 605 disposed offset from a center optical axis 610 of eye 100 to leverage a natural reflex of iris 110 to ambient light, in accordance with an embodiment of the disclosure. Iris 110 operates to moderate the dynamic range of illumination entering the eye by adjusting its aperture size in response to ambient illumination. Decentering optical tap 605 from center optical axis 610 through iris 110 accentuates this effect on optical tap 605, thus reducing the dynamic range experienced by the image sensor. In other words, decentering optical tap 605 within ophthalmic device 600 effectively reduces the numerical aperture of the image sensor and damps variations in illumination of the photosensors, which can reduce the burdens on the signal processing circuitry within controller 220.

Figure 7:
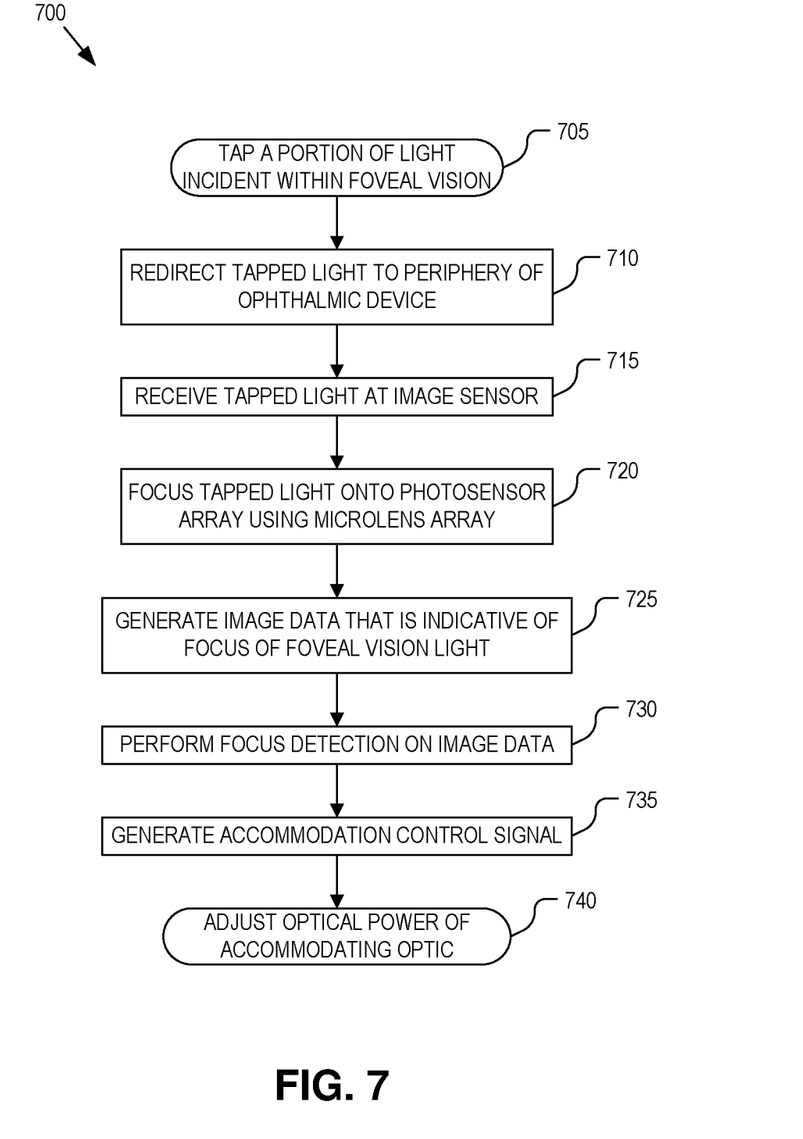
FIG. 7 is a flow chart illustrating a process of operation of an ophthalmic device to provide accommodative feedback control to an accommodating optic of an ophthalmic device, in accordance with an embodiment of the disclosure.

FIG. 7 is a flow chart illustrating a process 700 of operation of an ophthalmic device (e.g., IOLs 105, 605, or contact lens 115) to provide accommodative feedback control to an accommodating optic, in accordance with an embodiment of the disclosure. Process 700 is described with reference to FIG. 2A for convenience, but is equally applicable to all configurations described herein. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel.

In a process block 705, foveal vision light 127 incident into eye 100 is tapped by optical tap 210 and redirected to a periphery of the ophthalmic device (process block 710). In a process block 715, tapped light 240 is received at image sensor 215, where microlens array 225 focus tapped light 240 on photosensor array 230 (process block 720). In response to incident tapped light 240, photosensitive array 230 generates image data 250, which is indicative of a level of focus or defocus of foveal vision light 127 (process block 725). Controller 220 performs a focus detection scheme (e.g., phase-detect autofocus, contrast-detect autofocus, etc.) on image data 250 (process block 730) and generates accommodation control signal 255 based upon the level of focus/defocus calculated (process block 735). In one embodiment, the phase detection calculation analyzes relative intensities measured by the odd and even photosensors in photosensor array 230. For example, each microlens can split the pupil plane such that a shift between the light passing through a first half of the plane and creating an image on the left photosensor versus the light passing through a second half of the plane and creating an image on the right photosensor is indicative of defocus. Finally, in a process block 740, accommodating optic 205 adjusts its optical power in response to accommodation control signal 255.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device, comprising:
an accommodating optic having adjustable optical power;
an optical tap positioned within a vision of an eye when the ophthalmic device is mounted in or on the eye, wherein the optical tap is configured to redirect a portion of vision light that passes through the accommodating optic as tapped light, wherein the optical tap includes at least one of a diffractive optic, a refractive optical element, or a reflective optical element;
an image sensor positioned outside of a foveal vision of the eye when the ophthalmic device is mounted in or on the eye, the image sensor aligned to receive the tapped light from the optical tap and adapted to generate image data indicative of a focus of the vision light in response to the tapped light; and
a controller coupled to the accommodating optic and the image sensor, the controller adapted to generate an accommodation control signal for manipulating the adjustable optical power of the accommodating optic based upon the image data.

2. The ophthalmic device of claim 1, wherein the vision comprises the foveal vision and the vision light comprises foveal vision light.

3. The ophthalmic device of claim 2, wherein the optical tap comprises the diffractive optic.

4. The ophthalmic device of claim 3, wherein the diffractive optic is a notch filter tuned to redirect the portion of the foveal vision light having wavelengths coinciding with an absorption band of M-cone photoreceptor cells while substantially not redirecting other visible spectrum wavelengths.

5. The ophthalmic device of claim 3, wherein the image sensor comprises:
a first sensor submodule positioned to receive a positive diffraction order of the tapped light; and
a second sensor submodule positioned to receive a negative diffraction order of the tapped light, wherein the first and second sensor submodules are physically offset from each other.

6. The ophthalmic device of claim 2, wherein the optical tap has a first field of view (FOV) that is equal to or less than twice a second FOV of the foveal vision of the eye.

7. The ophthalmic device of claim 2, wherein the optical tap redirects the portion of the foveal vision light and includes fixed optical power.

8. The ophthalmic device of claim 1, wherein the image sensor comprises:
a photosensor array to generate the image data indicative of an intensity of the tapped light; and
a microlens array aligned to receive the tapped light from the optical tap and focus the tapped light onto the photosensor array, wherein the focus of the vision light correlates to a relative intensity of the tapped light sensed between photosensors within the photosensor array.

9. The ophthalmic device of claim 8, wherein the photosensor array and the microlens array each comprise a linear array, and wherein the photosensor array and the microlens array are aligned parallel to each other.

10. The ophthalmic device of claim 9, wherein the photosensor array and the microlens array each comprise a stacked linear array.

11. The ophthalmic device of claim 8, wherein a first numerical aperture of each microlens within the microlens array substantially matches a second numerical aperture of the optical tap.

12. The ophthalmic device of claim 1, wherein the optical tap is positioned within the ophthalmic device to be offset from a center optical axis passing through a center of an iris of the eye when the ophthalmic device is mounted in or on the eye.

13. The ophthalmic device of claim 1, wherein the optical tap comprises one of the refractive optical element or the reflective optical element.

14. The ophthalmic device of claim 1, wherein the optical tap is positioned optically behind the accommodating optic to provide closed loop feedback control over the accommodating optic.

15. The ophthalmic device of claim 1, wherein the ophthalmic device comprises an intraocular lens.

16. A method of operation of an ophthalmic device, the method comprising:
receiving foveal vision light of an eye through an accommodating optic having adjustable optical power;
redirecting a portion of the foveal vision light that passes through the accommodating optic as tapped light directed towards an image sensor, wherein the tapped light is redirected to a direction different than that of the foveal vision light;
generating image data with the image sensor in response to the tapped light, wherein the image data is indicative of a focus of the foveal vision light; and
adjusting the adjustable optical power of the accommodating optic based upon the image data to improve a focus of the foveal vision light for the eye.

17. The method of claim 16, wherein redirecting the portion of the foveal vision light comprises diffracting the portion of the foveal vision light with a diffractive optic.

18. The method of claim 17, wherein diffracting the portion of the foveal vision light comprises diffracting the portion of the foveal vision light having wavelengths coinciding with an absorption band of M-cone photoreceptor cells of the eye while substantially not redirecting other visible spectrum wavelengths.

19. The method of claim 17, wherein the image data with the image sensor comprises:
generating first image data with a first sensor submodule positioned to receive a positive diffraction order of the tapped light; and
generating second image data with a second sensor submodule positioned to receive a negative diffraction order of the tapped light.

20. The method of claim 16, further comprising:
leveraging a natural reflex of an iris of the eye to ambient light to reduce a dynamic range of illumination of the tapped light incident upon the image sensor by redirecting the portion of the foveal vision light with an optical tap positioned offset from a center optical axis passing through a center of the iris.

21. The method of claim 16, wherein redirecting the portion of the foveal vision light as tapped light directed towards the image sensor comprises:
redirecting the portion of the foveal vision light with an optical tap having a first field of view (FOV) that is equal to or less than twice a second FOV of the foveal vision.

22. The method of claim 16, wherein adjusting the adjustable optical power of the accommodating optic comprises closed loop feedback control over the accommodating optic.

23. The method of claim 16, wherein the ophthalmic device comprises an intraocular lens or a contact lens.

24. An ophthalmic device, comprising:
an accommodating optic having adjustable optical power;

an optical tap positioned within a vision of an eye when the ophthalmic device is mounted in or on the eye, wherein the optical tap is configured to redirect a portion of vision light that passes through the accommodating optic as tapped light, wherein the optical tap has a first field of view (FOV) that is equal to or less than twice a second FOV of a foveal vision of the eye;

an image sensor positioned outside of the foveal vision of the eye when the ophthalmic device is mounted in or on the eye, the image sensor aligned to receive the tapped light from the optical tap and adapted to generate image data indicative of a focus of the vision light in response to the tapped light; and a controller coupled to the accommodating optic and the image sensor, the controller adapted to generate an accommodation control signal for manipulating the adjustable optical power of the accommodating optic based upon the image data.

25. An ophthalmic device, comprising:

an accommodating optic having adjustable optical power;

an optical tap positioned within a vision of an eye when the ophthalmic device is mounted in or on the eye, wherein the optical tap is configured to redirect a portion of vision light that passes through the accommodating optic as tapped light;

an image sensor positioned outside of a foveal vision of the eye when the ophthalmic device is mounted in or on the eye, the image sensor aligned to receive the tapped light from the optical tap and adapted to generate image data indicative of a focus of the vision light in response to the tapped light; and a controller coupled to the accommodating optic and the image sensor, the controller adapted to generate an accommodation control signal for manipulating the adjustable optical power of the accommodating optic based upon the image data, wherein the vision comprises the foveal vision and the vision light comprises foveal vision light, and wherein the optical tap redirects the portion of the foveal vision light and includes fixed optical power.

* * * * *